United States Patent [19]

Kaule

[11] 4,046,477
[45] Sept. 6, 1977

[54] INTERFEROMETRIC METHOD AND APPARATUS FOR SENSING SURFACE DEFORMATION OF A WORKPIECE SUBJECTED TO ACOUSTIC ENERGY

[75] Inventor: Walter Kaule, Cologne, Germany

[73] Assignee: Krautkramer-Branson, Incorporated, Stratford, Conn.

[21] Appl. No.: 629,062

[22] Filed: Nov. 5, 1975

[30] Foreign Application Priority Data

Dec. 4, 1974 Germany .............................. 2457253

[51] Int. Cl.² .................................................. G01B 9/02
[52] U.S. Cl. .................................. 356/109; 73/67.5 R; 73/71.3
[58] Field of Search .......................... 356/106 R, 109; 73/67.5 R, 71.3

[56] References Cited

U.S. PATENT DOCUMENTS

| | | | |
|---|---|---|---|
| 3,319,515 | 5/1967 | Flournoy | 356/108 |
| 3,503,012 | 3/1970 | Gillard | 356/106 R X |
| 3,535,024 | 10/1970 | Schindler | 356/106 R X |
| 3,633,987 | 1/1972 | Brooks | 356/109 X |
| 3,822,942 | 7/1974 | Hock | 356/106 R |

*Primary Examiner*—John K. Corbin
*Assistant Examiner*—Matthew W. Koren
*Attorney, Agent, or Firm*—Ervin B. Steinberg; Philip J. Feig

[57] ABSTRACT

In contact-free testing a workpiece by ultrasonic energy an interferometric method and apparatus is used to sense acoustic energy by determining the deformation of a workpiece surface while such workpiece is undergoing acoustic exploration. The surface of the workpiece is illuminated by a laser beam which is reflected thereat and reaches an optical beam splitter to produce a measuring beam portion and a reference beam portion. The measuring beam portion after reflection at a mirror is transmitted to photoelectric means, while the reference beam portion is time delayed via an optical delay path and then brought to interfere with the measuring beam portion at the photoelectric means.

18 Claims, 6 Drawing Figures

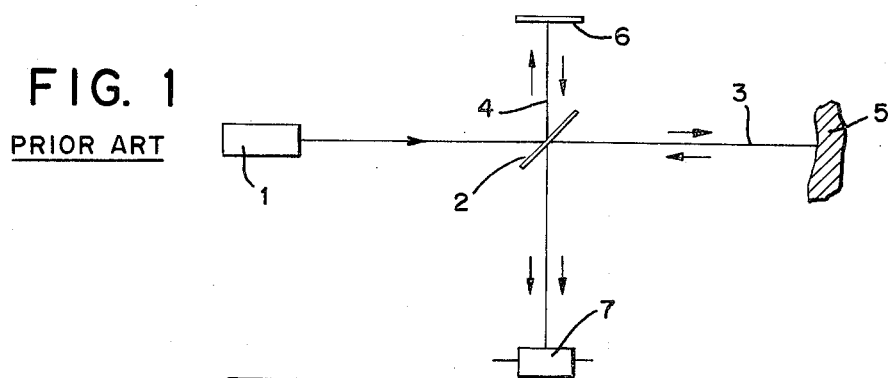
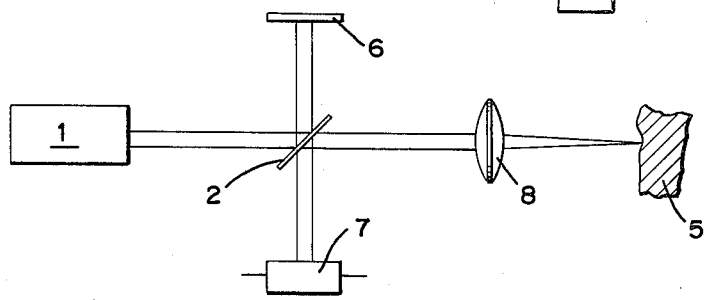
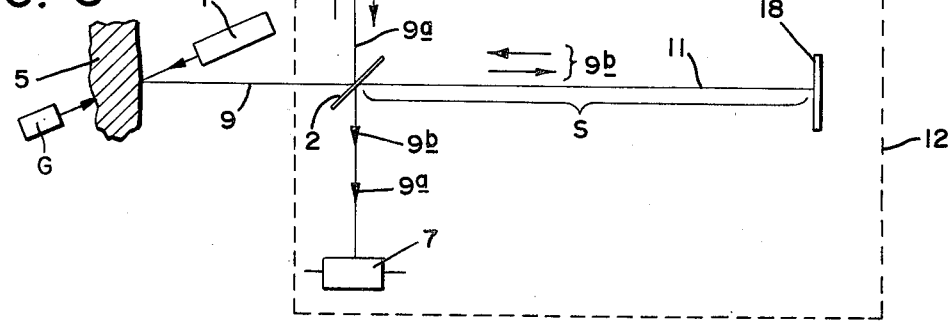
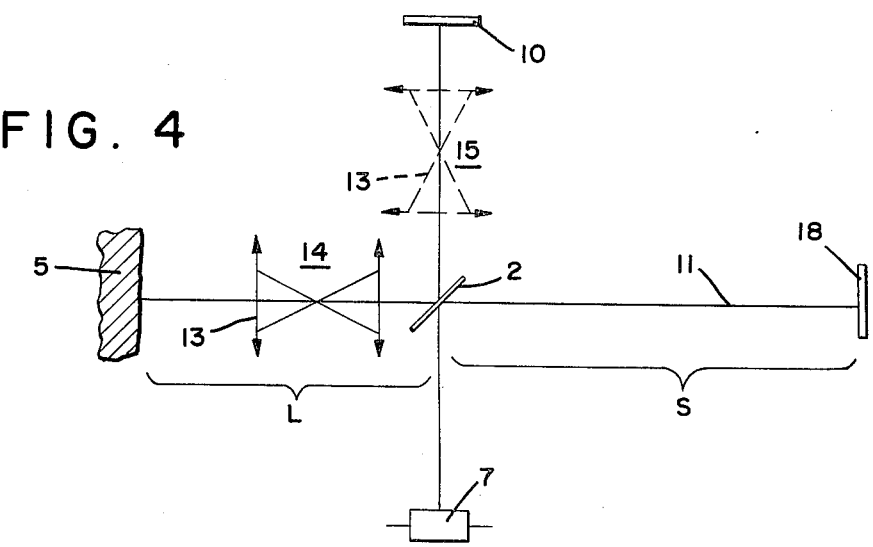

INTERFEROMETRIC METHOD AND APPARATUS FOR SENSING SURFACE DEFORMATION OF A WORKPIECE SUBJECTED TO ACOUSTIC ENERGY

BRIEF SUMMARY OF THE INVENTION

This invention concerns an optical interferometric method for sensing the surface deformation of an object (workpiece) wherein such motional deformation is caused by subjecting the workpiece to ultrasonic energy and, more specifically, refers to the contact-free reception of ultrasonic energy utilizing a light beam which by means of an optical beam splitter is divided into a measuring beam and a reference beam. An optical arrangement of this type is particularly suited for testing workpieces which are at a greatly elevated temperature or workpieces, such as plate stock, which pass through a test station at a high translational speed. The invention, therefore, is useful in connection with automatic test apparatus in which contact-free testing of workpieces, typically of plate stock, of hot workpieces, or of rapidly moving workpieces, is to be accomplished.

Contact-free reception of ultrasonic waves is possible only if the deformation of the workpiece surface responsive to the sonic energy is sensed optically. The deformation is small and amounts to about ten nanometers or less, assuming the frequency and amplitude range generally used for testing workpieces by ultrasonic energy. In order to determine these rather small deformation interferometric methods are necessary.

When testing workpieces in a conventional manner by ultrasonic energy most commonly piezoelectric transducers are used for receiving the ultrasonic energy. The transducers must be coupled to the workpiece via a coupling medium which transmits the sound pressure and, hence, physical contact between the transducer and the workpiece is a prerequisite.

This requirement gives rise to difficulties when testing hot workpieces or workpieces passing through an automatic test station at high speed. For this reason and to eliminate direct contact with the workpiece magnetic or electrostatic methods have been proposed for receiving the ultrasonic energy. Because of the steep decrease of the signal intensity as a function of distance inherent in the stated methods, the respective receive probes must be disposed within a fraction of a millimeter from the workpiece surface and even then, these probes are less sensitive than a piezoelectric transducer. The described difficulties are not eliminated by the use of the so-called dry methods. Furthermore, it is known to use interferometers, e.g. Michelson method, for measuring the motion of the surface of a workpiece as a function of spacing relative to a reference surface.

In accordance with the present invention the disadvantages described above are overcome by illuminating the surface of the workpiece directly with a monochromatic coherent light beam, particularly a laser beam. After splitting the reflected light beam, one beam portion is utilized as a measuring beam and transmitted to the light receiver, whereas the other beam portion, used as a reference beam, is transmitted over a delay path (thus having a greater path length than that of the measuring beam) and subsequently transmitted to the same light receiver and brought to concidence upon the first stated beam forming the main beam. This method results in an arrangement for sensing the deformation of a workpiece surface responsive to ultrasonic energy wherein the reference beam no longer is reflected on a plane mirror surface as in prior arrangements, but on the same surface as is the measuring beam.

In this manner both beams within the field of view exhibit always the same phase relationship. Stated in other words, the reference beam is reflected at the same surface portion as is the measuring beam, however, the reference beam is delayed by a time interval selected to be a function of the ultrasonic frequency whereby to cause the surface portion to be imaged in the image plane of an interferometer by the main beam (measuring beam) as well as by the reference beam, superposed with one another. This method is applicable also to rough surfaces.

A principal object of this invention, therefore, is the provision of a new and improved sensing method useful for ultrasonic testing of workpieces.

Another object of the present invention is the provision of an optical interferometric method for sensing without physical contact the surface deformation of a workpiece subjected to ultrasonic energy.

Still another object of the present invention is the provision of an optical interferometric method for sensing surface deformation of a workpiece subjected to ultrasonic energy wherein the reference light beam is transmitted over a predetermined delay path before being brought to coincidence with the measuring beam for reforming the original beam.

A further object of the present invention is the provision of an optical interferometric apparatus using monochromatic light for sensing surface deformation of a workpiece subjected to ultrasonic energy, the apparatus being useful also for workpieces having a rough surface.

Further and still other objects of this invention will become more clearly apparent when the specification is read in conjunction with the accompanying drawings.

BRIEF DESCRIPTION OF THE DRAWINGS

FIG. 1 is a schematic diagram showing a prior art interferometer arrangement;

FIG. 2 is a schematic diagram showing another prior art interferometer arrangement with a lens system;

FIG. 3 is a schematic diagram showing an interferometric arrangement in accordance with the present invention;

FIG. 4 is a schematic diagram showing an interferometric arrangement per FIG. 3, but including a lens system;

DETAILED DESCRIPTION OF THE INVENTION

Figures 5, 6:
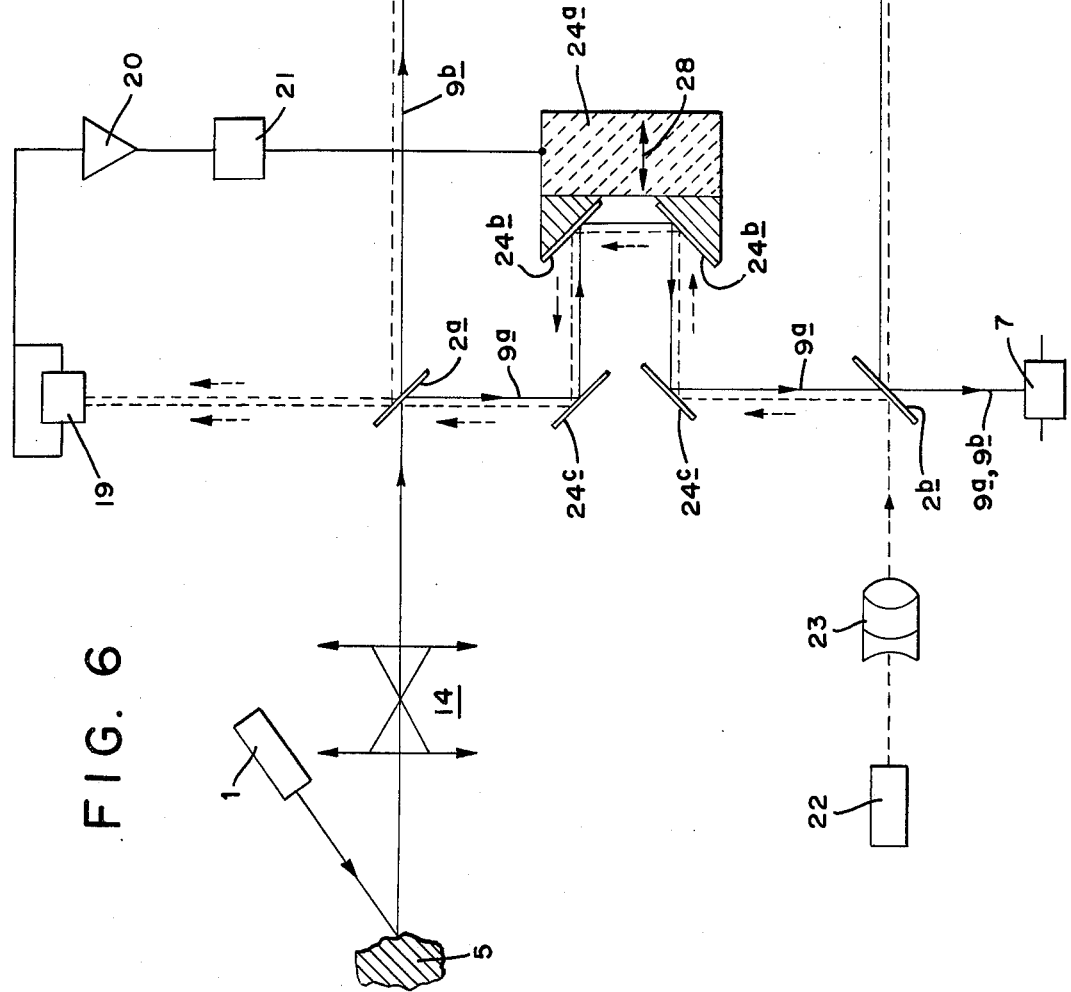
FIG. 5 is a schematic diagram showing a modification of the interferometric arrangement.
FIG. 6 is a schematic diagram showing a second interferometer for measuring the length of the light path and developing a control signal to provide correction.

FIG. 1 shows a prior art interferometer arrangement. Monochromatic coherent light produced, for example, by an optical laser beam source 1 is split by means of a beam splitter 2 (semi-transparent mirror) into two coherent light beams 3 and 4. One beam is incident upon the vibrating surface of a workpiece 5 and the other upon the reference mirror 6. After reflection, both beams are combined by the optical beam splitter 2 and caused to interfere on the photoelectric means or photocell 7. The resulting degree of illumination measured by the photocell 7 is dependent upon the relative phase of both light beams. Depending upon the motion of the surface of the workpiece 5, the phase of the reflected light beam changes and, hence, also the relative phase relation between the measuring beam 3 and the reference beam 4. This arrangement causes a change in light intensity at the photocell 7 and causes a corresponding change of the electric signal produced by the photocell 7. A prerequisite of the measuring system is that the illumination level changes uniformly over the entire light receiving surface of the photocell 7. Additionally, the phase difference between both light beams over the entire light receiving surface must remain constant. This condition is assured if the measuring light beam and the reference beam form at the photocell 7 an angle $\alpha$ for which the condition applies:

$$\alpha << \lambda/2/d$$

wherein
$\lambda$ = wavelength of the laser light
$d$ = diameter of the photocell An interferometric measurement of this type can be made only on mirrored surfaces which form with the measuring beam the same angle as that of the reference mirror with the other beam, i.e. the reference beam.

The interferometric measurement is not possible on greatly irregular surfaces prevalent when testing workpieces since the phase of the reflected signal varies non-uniformly within the viewing angle and, therefore, causes a non-uniform light intensity incident upon the light receiving surface of the photocell. In this event it is possible, however, as shown in FIG. 2, to cause the surface 5 to be disposed at the focal point of a lens 8. In this manner, a point at the vibrating surface of the workpiece 5 is illuminated and the diffused reflected light, after passing through the lens, is directed along a parallel path. The measuring beam once again is incident upon the photocell 7 in the form of a plane wave and thus fulfills at the flat mirror 6, serving as the reference surface, the required condition:

$$\alpha << \lambda/2/d$$

The above described arrangement when used for testing workpieces exhibits, however, the following disadvantages.

A precise guiding of the workpiece surface 5 under test is required in order to retain this surface at all times at the focal point of the lens 8. A deviation from such position causes an additional and undesired light intensity modulation. It is most difficult to achieve such a precise motion of the translating workpiece. Moreover, the roughness of the workpiece surface is also scanned and such unevenness produces a further undesired light intensity modulation having an interfering frequency. The test speed, therefore, is limited to a few millimeters per second. A further disadvantage resides in the fact that an uneven reflection characteristic at the workpiece surface causes nonuniform amplitudes of the measuring and of the reference beams. Also, a sharp focal point is required, necessitating, in view of the conditions inherent in the optical imaging, measuring distances in the order of ten centimeters. Such small measuring distances, in practice, severely limit the application of the known methods. Finally, acoustic energy is received from only one point along the surface, whereas an integrated value representing a larger area, approximately corresponding to that of a conventional test probe, is desired.

IMPROVED ARRANGEMENT

The principle of the present interferometric method is best shown in FIG. 3. It should be observed that in a practical embodiment certain changes in the general arrangement are necessary in order to avoid interference from light leakage, etc. The workpiece 5 is subjcted to acoustic energy, either pulse or continuous wave energy, by a laser beam or other conventional source of acoustic energy G, typically having a frequency in the range from 1 to 10 MHz, not shown. The surface of the workpiece 5 at which the acoustic energy induced surface deformation is to be sensed is illuminated by monochromatic light produced by a laser beam source 1. The use of a laser source is not only advantageous in view of the monochromatic light produced, but also by virtue of the fact that the light comprises a collimated beam. The reflected light beam 9 is transmitted to the beam splitter 2 and is transmitted from there as a main beam portion 9a to the mirror 10 where it is reflected and returned once again to the beam splitter 2 and provided to the photocell 7. The other light beam portion 9b produced at the beam splitter 2 is caused to travel through a delay path 11 having the form of a folded optical path between the beam splitter 2 and a reflecting mirror surface 18, the total travel distance being two times S. Hence, beam portion 9b is caused to arrive at the photocell 7 delayed in time with respect to the beam portion 9a and, thus is delayed relative to the main (measuring) beam 9a. When subjecting the surface 5 to acoustic energy, the measuring beam 9a is subjected also to an additional phase shift corresponding to the workpiece surface deflection occurring within the time delay interval. In this manner, the resulting illumination incident upon the photocell 7 varies. For a given acoustic frequency the signal amplitude at the photocell is at a maximum when the half period of the acoustic energy induced mechanical vibration equals the delay time. In this manner, the present arrangement is rendered selective for a predetermined frequency range, while being nonresponsive to low frequencies whose half period of vibration is large relative to the delay time.

The optimum length S of the delay distance 11 is given by two conditions:

1. Macroscopically the length S of the delay path must be selected to obtain the previously indicated suitable delay time equal to one half the period of the mechanical vibration; and 2. Microscopically the length S must be adjusted to produce, responsive to the interference with the measuring beam 9a, an illumination magnitude at the photocell 7 which provides well recognizable illumination changes responsive to the occurrence of small phase changes.

A rough workpiece surface 5 produces a diffused light reflection. In order to retain the condition $$\alpha << \lambda/2d$$

at the photocell 7, a small angular region of the reflected light beam must be masked out. The light beam should not be divergent along the path between the beam splitter 2 and the photocell 7 within the optical receiving system 12, see FIG. 3. This condition is achieved by employing the means shown more clearly in FIG. 4.

The possibility of making the light beams sufficiently parallel comprises adjusting the length of the distance L, measured from the workpiece surface 5 to the beam splitter 2, to a value which is at least five times the length of the distance S, which presupposes a reasonable magnitude of the receiving surface 7, maximum 1 square centimeter. The same result is achieved by a telescopic lens system having disposed in its common focal point an aperture of suitable magnitude typically 50 to 100 μm. A typical lens arrangement comprises two lenses each 10 to 20 mm diameter, 250 mm focal length. The lens assembly operates in the manner of a directional filter 13 which can be disposed within the region 14 between the workpiece surface 5 to be sensed and the beam splitter 2, or within the region 15 between the beam splitter 2 and the mirror surface 10. In a practical embodiment, the light path necessary for obtaining a delay can be achieved within a small amount of space using multiple light reflection between a pair of facing, high precision flat mirrors 16 and 17, see FIG. 5.

To provide for the sensing of small deformations of the workpiece, which are in the order of a few nanometers, the length of the delay path S must be kept precisely at an optimum value. This is necessary to avoid illumination variations resulting from phase shifts caused by changes of the light path length in the delay path. To accomplish this, the length S of the delay path 11 can be measured by a second interferometer, not shown in FIG. 3. For the purpose of this interferometer a portion of a light from laser 1 or a separate laser source is used. Only a small amount of light energy is needed since plane and high reflective mirrors can be utilized.

If the distance S deviates from the prescribed value, the mirror 18 is displaced or moved by means of a piezoelectic element or other suitable adjusting means coupled to the mirror 18, see for instance, U.S. Pat. No. 3,899,921, Hockley, dated Aug. 19, 1975.

In a further modification, the length S is modulated by the above stated adjusting means (piezoelectric means) at a frequency $f_1$ which is selected to be larger than the acoustic frequency $f_2$ to be sensed. The optimum path difference between the measuring beam and the reference beam then occurs several times within the vibration period of the acoustic energy wave. In the latter embodiment, the electrical signal appearing at the photocell 7 is a high frequency signal appearing at the photocell 7 is a high frequency signal at the frequency $f_1$ modulated by the frequency $f_2$ of the acoustic energy wave.

It will be apparent that by suitable calibration methods, the electrical signal developed at the photoelectric means 7 can be used to measure the actual amount of deformation occurring at the workpiece surface. Moreover, as in pulse-echo defect testing, the time interval between the applied elastic deformation and the sensed deformation serves as a measure of the distance from the location at which the wave energy entered the workpiece to an acoustic discontinuity.

The use of a second inteferometer is shown in FIG. 6, using dashed lines for the light beam from the second interferometer. As contrasted with the description hereinbefore in which the length of the delay path was varied, in the following embodiment the length of the nondelayed light path 9a is adjusted to compensate for dimensional changes of the system as sensed by the second interferometer. It is apparent that either one of the two light paths can be adjusted for providing compensation resulting from dimensional changes of one of the paths. The aim is to obtain constant illumination level at the photocell associated with the second interferometer.

A pair of mirrors 24b are rigidly coupled to a piezoelectric element 24a which is controlled by an electrical signal from an auxiliary photocell 19 via an amplifier 20 and a low-pass filter 21. The piezoelectric element is used to change the spacing between the mirrors 24b and the fixed mirrors 24c, see arrow 28.

The laser 1, as described above, illuminates a surface portion of workpiece 5 from where a reflected light beam is directed via the lens system at location 14 to a beam splitter 2a. The measuring beam portion 9a is reflected toward the upper mirror in a set of mirrors 24c, the upper mirror in a set of mirrors 24b, the lower mirror 24b, the lower mirror 24c, and through a further beam splitter 2b to the photocell 7. The reference beam 9b after reaching the beam splitter 2a follows the delay path toward the mirror 18a, mirror 18b, and beam splitter 2b toward the photocell 7.

The interferometric arrangement for determinining the change in length of the delay path comprises an auxiliary laser 22 which via a lens system 23, a beam expander, propagates its beam toward the beam splitter 2b. A first beam portion generated by the splitter 2b is reflected toward the lower mirror 24c, lower mirror 24b, upper mirror 24b, upper mirror 24c and through the splitter 2a toward the auxiliary photocell 19. The other beam portion, after leaving splitter 2b, is reflected at mirror 18b, mirror 18a, beam splitter 2a and also reaches photocell 19.

Without an external disturbance a predetermined illumination level is present at the auxiliary photocell 19. In the event of a disturbance which causes a change of the distance of the delay path along mirrors 2a, 18a, 18b, and 2b, a change of illumination is noted at photocell 19. This change is manifest as a change in the magnitude of the electrical signal provided by the photocell. The signal acts upon piezoelectric element 24a via amplifier 20 and filter 21 for causing motion of mirrors 24b so as to restore the original value of illumination at the photocell 19. Hence, the disturbance affecting the delay path between mirrors 2a and 2b is compensated. This compensation also restores the original phase relation between the measuring beam portion 9a and the reference beam portion 9b. As shown in FIG. 4, the delay path can be physically shortened by multiple reflection between a set of mirrors.

By virtue of the low-pass filter 21, the piezoelectric element 24a receives a signal containing only the frequency corresponding to externally originating disturbances. As will be apparent to those skilled in the art, the two laser beams operate with light of different wavelength, e.g. argon and helium-neon respectively.

While in the foregoing description several preferred embodiments of the invention have been described, it will be apparent to those skilled in the art that further variations and modifications can be made without deviating from the broad principle of the present invention which shall be limited only by the scope of the appended claims.

What is claimed is:

1. The method of sensing by optical interference the deformation of a workpiece surface resulting from transmitting acoustic energy into the workpiece comprising:

applying to a workpiece acoustic wave energy for causing surface deformation on such workpiece;

transmitting a monochromatic beam of light upon the surface of the workpiece for sensing such deformation;

splitting said beam after reflection at said workpiece surface into a measuring beam portion and a reference beam portion;

transmitting said measuring beam portion to photoelectric sensing means, and transmitting said reference beam portion over a delay path and thereafter bringing said reference beam to coincidence with said measuring beam portion at said photoelectric means.

2. The method as set forth in claim 1, said monochromatic beam of light being generated by a laser.

3. The method as set forth in claim 2 and varying the distance of the delay path periodically from a predetermined value at a frequency $f_1$ which is higher than the frequency $f_2$ of the acoustic energy applied to the workpiece, thereby causing the electrical signal manifest at said photoelectric means to be responsive to the frequency $f_1$ modulated by the frequency $f_2$.

4. The method as set forth in claim 2, said delay path being in the form of a folded optical path beginning at the location where the beam is split, and dimensioning the distance traveled by the beam from the workpiece surface until being split to be at least five times the length of said delay path measured as the distance from the location at which the beam is split to the distal end of said folded path.

5. The method as set forth in claim 2 and disposing a telescopic lens system which includes an aperture at the common focal point in the beam path between the workpiece and the location at which said beam is split.

6. The method as set forth in claim 2 and disposing a reflecting mirror surface in the path of said measuring beam for directing said measuring beam toward said photoelectric means, and placing a directional filter in the path of said measuring beam between the location at which said beam is split and said mirror surface.

7. The method as set forth in claim 2, and including reflecting respectively said measuring beam portion and said reference beam portion at mirror means along their paths toward said photoelectric means; measuring the distance of said delay path for a deviation from a predetermined value, and providing compensation for such deviation by moving a respective mirror means.

8. An apparatus for sensing by optical interference the deformation of a workpiece surface resulting from acoustic energy applied to such workpiece comprising in combination:

means coupled for applying to a workpiece acoustic wave energy for causing surface deformation on such workpiece;

a source of laser beam disposed for directing its beam upon a surface portion of the workpiece for sensing such deformation;

an optical beam splitter;

an optial delay path and photoelectric sensing means so disposed that said laser beam responsive to being directed upon the surface portion of the workpiece and being reflected thereat reaches said beam splitter and a first measuring beam portion leaving said splitter is incident upon said sensing means, while a second beam portion leaving said splitter as a reference beam is transmitted over said delay path toward said sensing means for concidence with said first beam portion.

9. An apparatus as set forth in claim 8 and a first reflecting mirror disposed in the path of said first beam portion from said beam splitter to said sensing means.

10. An apparatus as set forth in claim 9, and a telescopic lens system which includes an aperture at the common focal point disposed in the path between said beam splitter and said first mirror.

11. An apparatus as set forth in claim 8, said delay path starting at said beam splitter and comprising a folded optical path with reflecting means disposed at the distal end of said delay path.

12. An apparatus as set forth in claim 11, and means coupled to said reflecting means for periodically varying the distance of said delay path from a predetermined value by displacing said reflecting means at a predetermined frequency of oscillation.

13. An apparatus as set forth in claim 12, said frequency of oscillation for varying the distance of said delay path being greater than the frequency of acoustic energy applied to the workpiece.

14. An apparatus as set forth in claim 8, and a telescopic lens system which includes an aperture at the common focal point disposed in the path between the workpiece surface and said beam splitter.

15. An apparatus as set forth in claim 8, the distance of the optical path from said workpiece surface portion to said beam splitter being greater than the distance of said delay path from said beam splitter to the distal end of said delay path.

16. An apparatus as set forth in claim 8, said optical path from said workpiece surface portion to said beam splitter being at least five times that of said delay path from said beam splitter to the distal end of said delay path.

17. An apparatus as set forth in claim 8, and including respective mirror means disposed in the path of said first beam portion and of said second beam portion along their respective paths from said beam splitter toward said photoelectric sensing means; means disposed for measuring the deviation of said delay path from a predetermined value, and means coupled to a selected one of said mirror means for moving said last-stated mirror means relative to a fixed reference responsive to such deviation.

18. An apparatus as set forth in claim 17, said means for measuring comprising a second laser beam source, a second photoelectric sensing means and means causing beam portions of said second laser to follow substantially the respective paths of said first and second beam portions to coincidence at said second sensing means, said second sensing means providing an electrical signal responsive to the illumination incident thereupon by the beam portions from said second laser source, and means causing said electrical signal to be applied as a control signal to piezoelectric means coupled to said mirror means.

* * * * *